United States Patent [19]

Wagner et al.

[11] Patent Number: 4,853,551
[45] Date of Patent: Aug. 1, 1989

[54] SAFETY INTERLOCK FOR X-RAY PARTICLE SIZE ANALYZER

[75] Inventors: Jack J. Wagner, Dunwoody; Samuel V. Tidwell, Norcross, both of Ga.

[73] Assignee: Micromeritics Instrument Corporation, Norcross, Ga.

[21] Appl. No.: 115,499

[22] Filed: Oct. 30, 1987

[51] Int. Cl.[4] .............................. H05G 1/02
[52] U.S. Cl. .................. 250/515.1; 378/160
[58] Field of Search .......... 250/515.1, 498.1; 378/160

[56] References Cited

U.S. PATENT DOCUMENTS

| | | | |
|---|---|---|---|
| 3,449,567 | 6/1969 | Olivier et al. | 378/51 |
| B1 3,449,567 | 10/1982 | Olivier et al. | 378/51 |
| 3,621,243 | 11/1971 | Olivier | 378/51 |
| B1 3,621,243 | 4/1983 | Olivier et al. | 378/51 |
| 3,697,755 | 10/1972 | Boisservain et al. | 378/160 |
| 4,100,419 | 7/1978 | Pedroso | 250/515.1 |

OTHER PUBLICATIONS

Brochure "Micromeritics SediGraph 5000ET Particle Size Analyzer", Form 501/42703/00, pages marked 00092–00099.
Brochure "Micromeritics SediGraph 5000ET Sedi-Comp", Form 501/42701/00, pages marked 00090–00091.
Instruction Manual Sedigraph 5000ET Particle Size Analyzer, P/N: 501/42805/03, Jan. 15, 1986, pp. 00001–00089.
Service Manual Micromeritics Sedigraph Model 5000ET, P/N 501/42806/00, pp. 00166–00413.
Instruction Manual Sedigraph 5000D Particle Size Analyzer, P/N: 500/42801/00, pp. 00422–00537.
Owner's Manual, "Microscan Particle Size Analyzer" MSC-1 (6/86).

Primary Examiner—Bruce C. Anderson
Assistant Examiner—Jack I. Berman
Attorney, Agent, or Firm—Jones, Askew & Lunsford

[57] ABSTRACT

An x-ray sedimentation particle size analyzer in which data is taken only at particular positions along the sedimentation cell, and each such position is individually calibrated. Presentation of the data in the form of a particle size distribution curve can be accomplished very accurately using interpolation techniques. The sedimentation cell design is free of the effects of undesirable density gradients, capable of detecting and removing bubbles, capable of attaining a highly uniform dispersion of sample prior to sedimentation, and including a safety interlock device for blocking x-ray projection when the cell is being accessed.

3 Claims, 6 Drawing Sheets

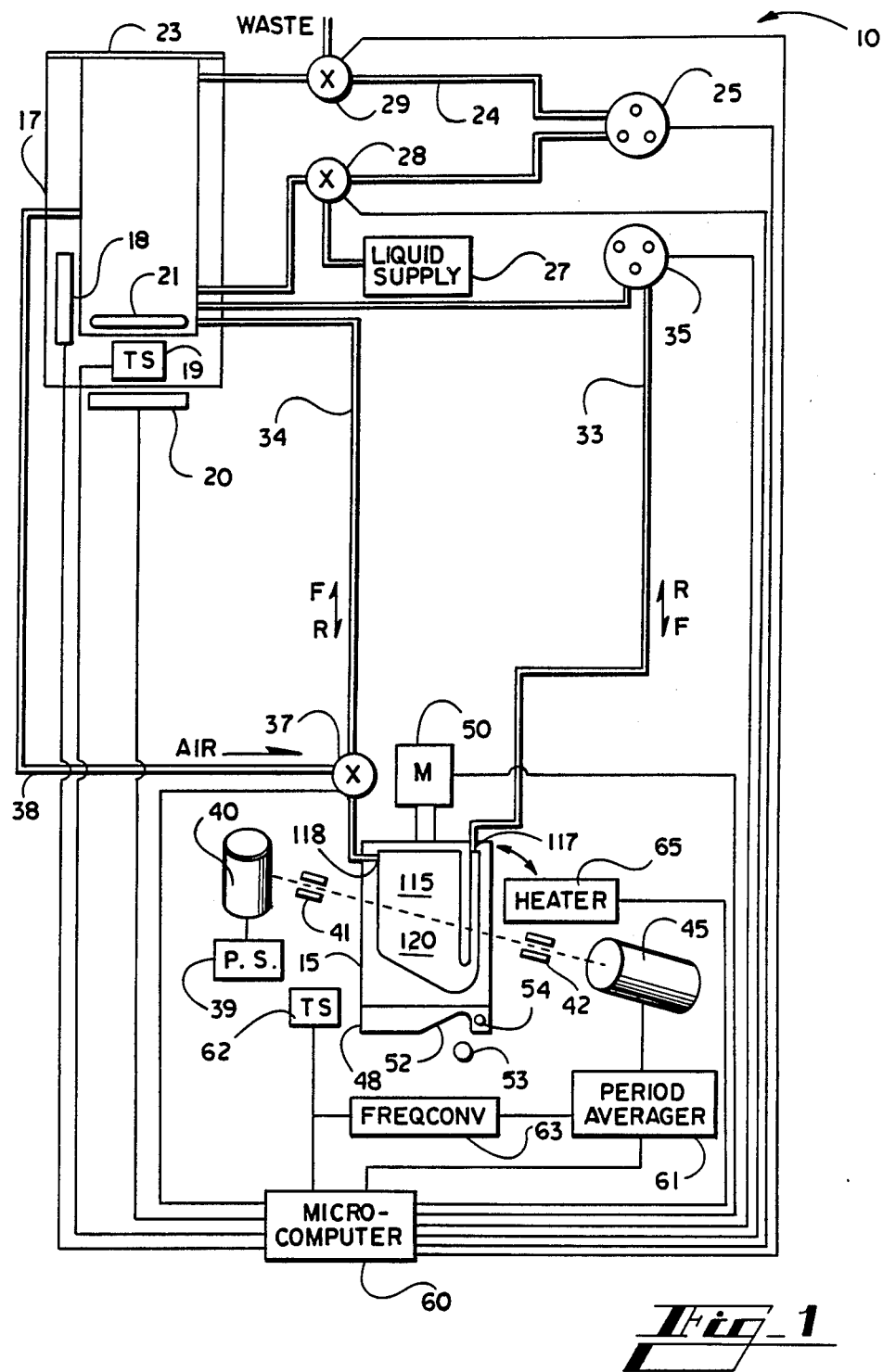
Fig_1

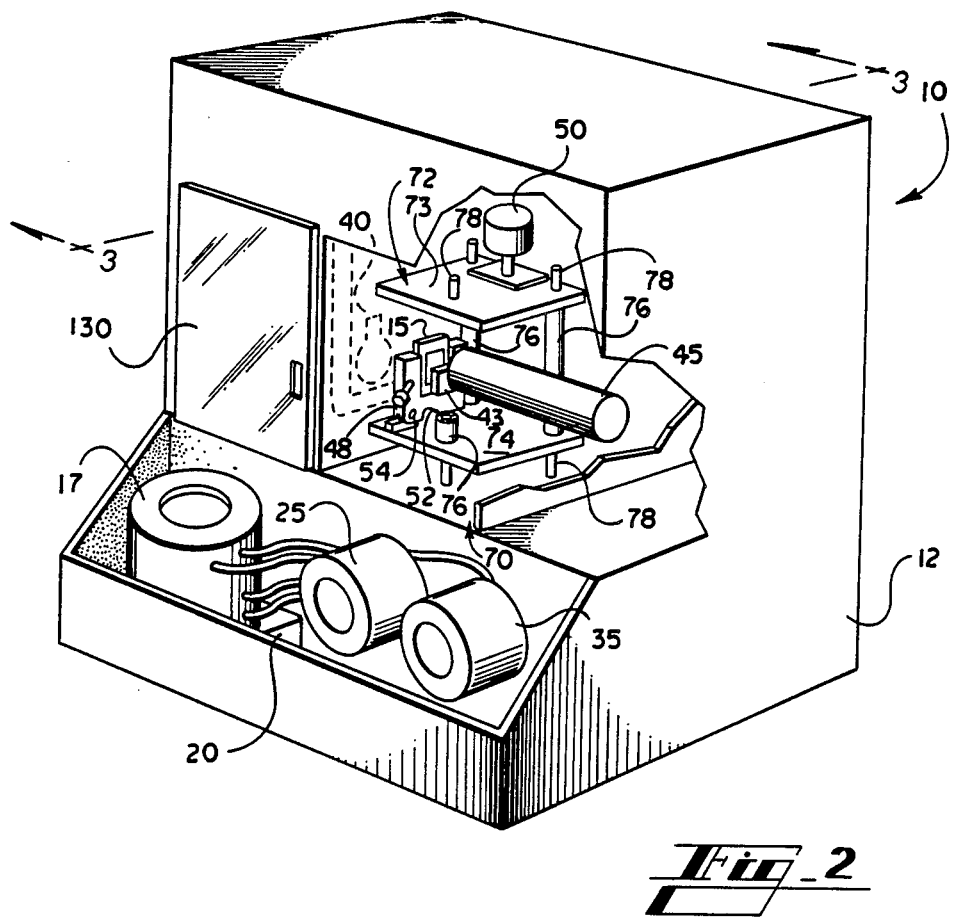
Fig_2

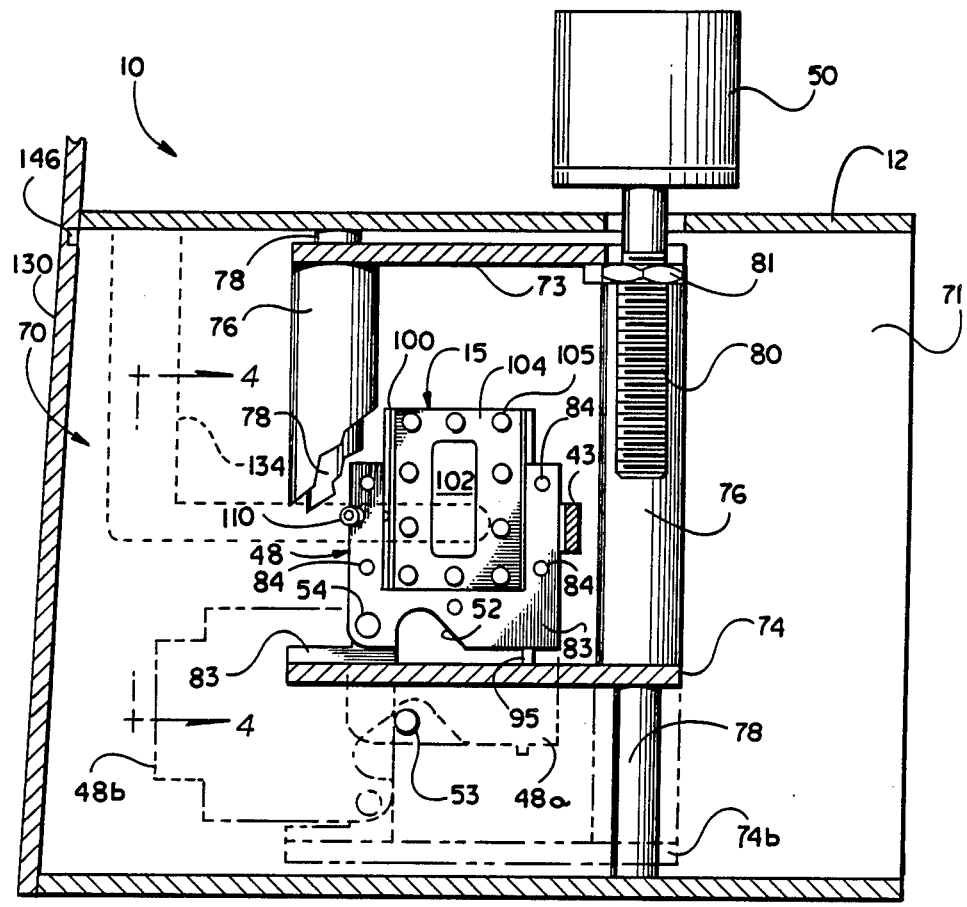
Fig_3

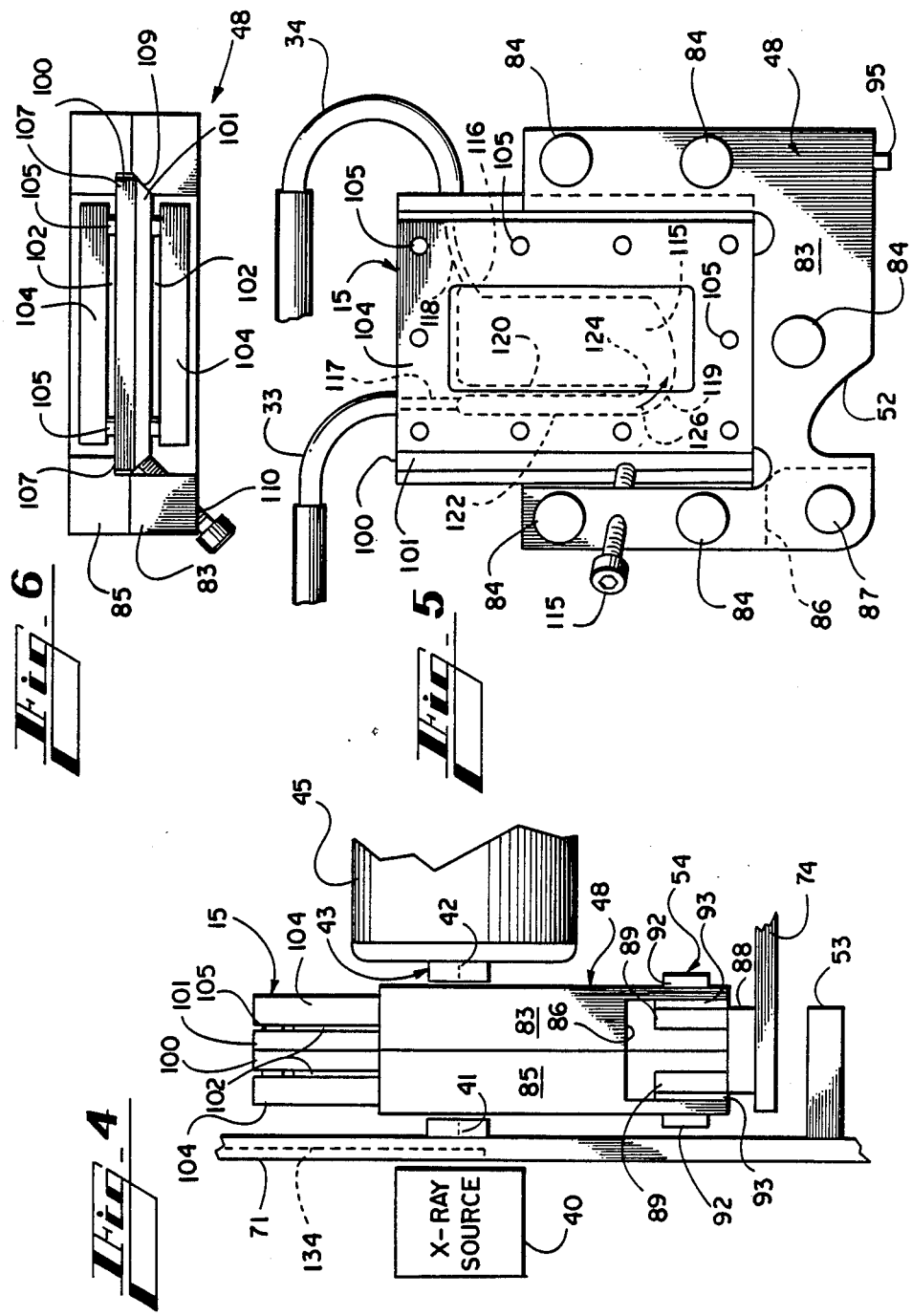

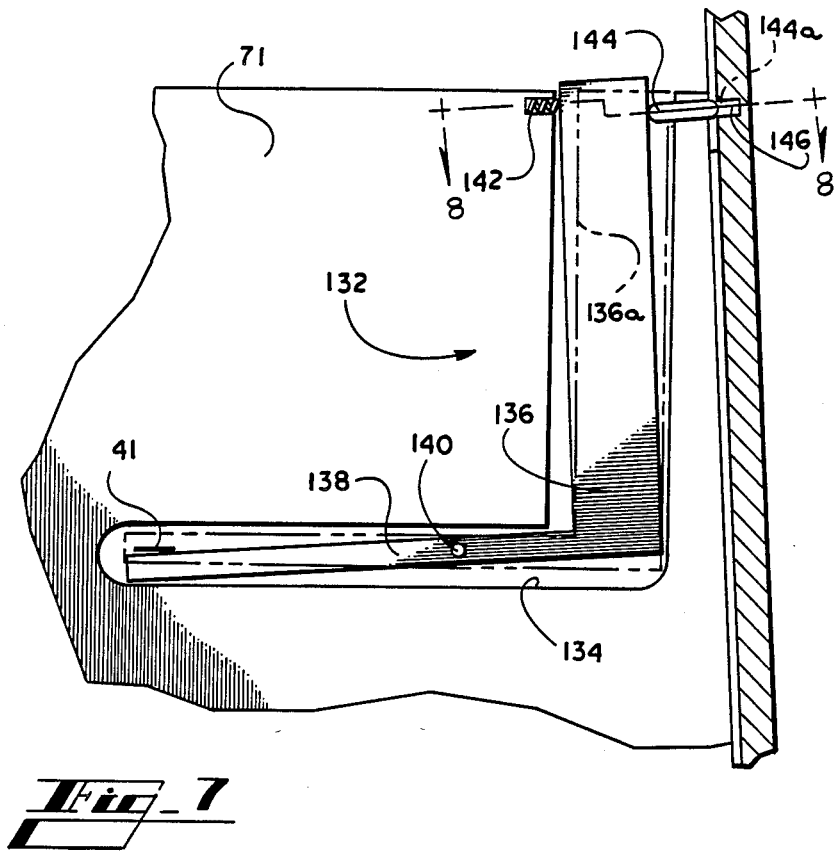
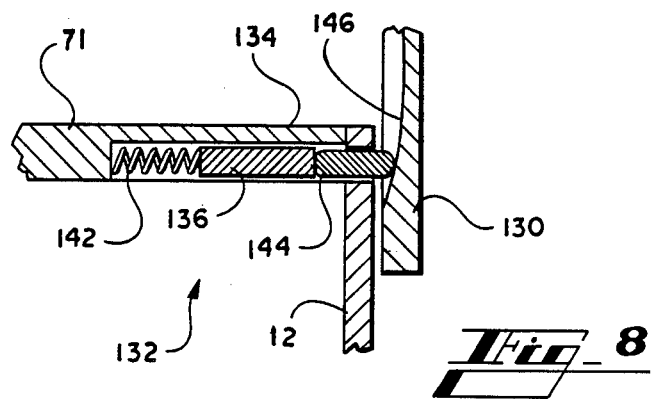

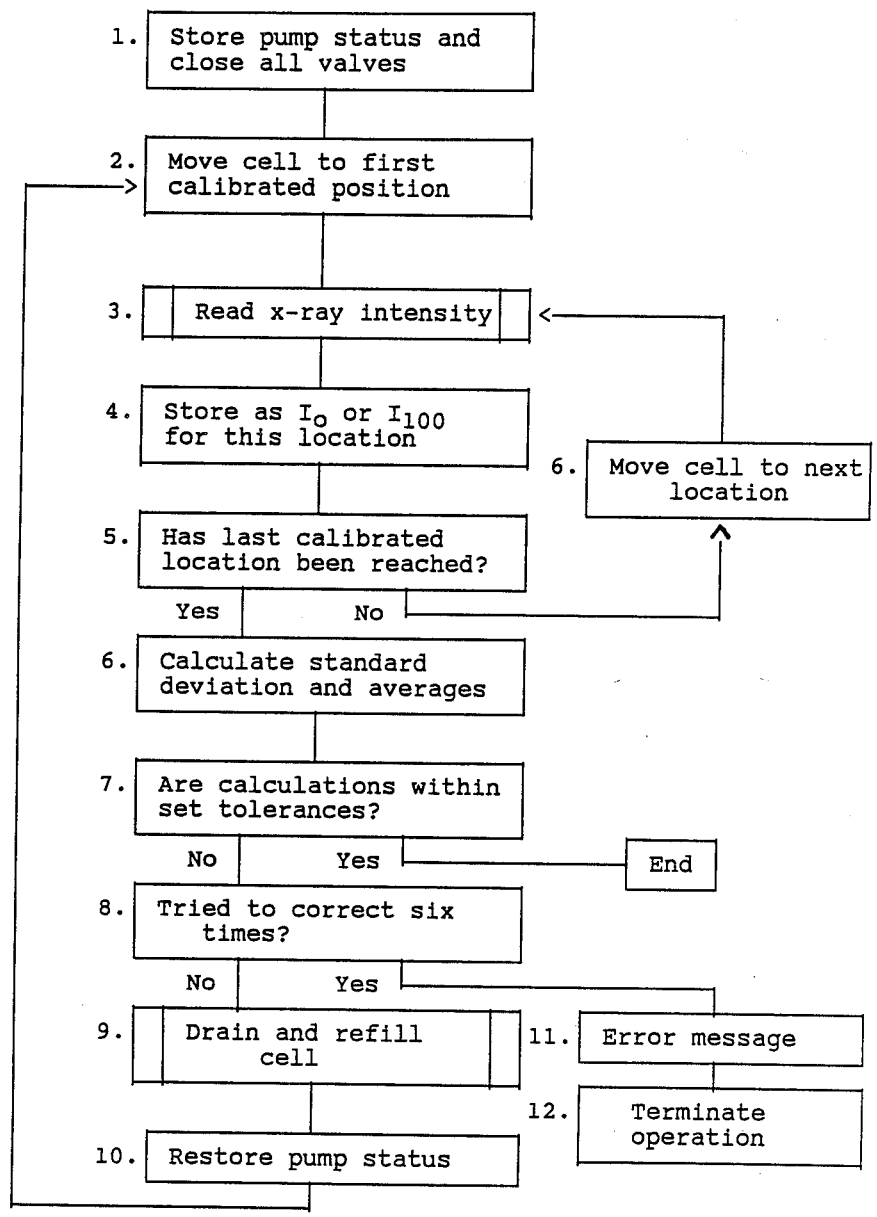

SAFETY INTERLOCK FOR X-RAY PARTICLE SIZE ANALYZER

TECHNICAL FIELD

The present invention relates to particle size analysis using Stokes' Law sedimentation techniques and x-ray absorption, and more particularly relates to such analysis in which the relative position of the x-ray beam and sample cell is changed during the analysis.

BACKGROUND ART

When using finely divided solids in industrial and scientific applications, it is often necessary to determine the distribution of the sizes of particles making up the sample. It may be critical, for example, that a catalyst be made up of particles at least a certain percentage of which by weight are smaller than a certain diameter. A typical manner in which particle size information is presented is the particle size distribution curve, which plots percent finer against particle size.

One widely used technique for determining particle size data uses Stokes' Law of sedimentation, which provides that at a given time after sedimentation of the sample suspended in a liquid has begun, particles larger than a given size will have fallen below a certain distance from the surface of the suspension. It follows that the percent of particles finer than the given size can be determined from the concentration of all particles at the certain distance. The transmission of x-rays through the suspension is a function only of the weight concentration of suspended solids, and therefore has provided the most convenient and accurate way to measure concentration in carrying out the sedimentation technique. Devices have been made using other electromagnetic radiation, such as visible light.

Significant economy in the time required for such an analysis was realized with the concept of continuously moving the sample cell and radiation source relative to one another during sedimentation while moving a pen plotting the particle size axis of the particle size distribution curve in a coordinated fashion to at all times satisfy Stokes' Law. This concept was disclosed in the early work of Muta, U.S. Pat. No. 3,315,066 and of Kalshoven, British Pat. No. 1,158,338. Subsequent improvements disclosed in U.S. Pat. Nos. 3,449,567 and 3,621,243 to Olivier and Hickin led to successful commercial embodiments, among them the Sedigraph 5000 series of instruments manufactured by Micromeritics Instrument Corporation. Detailed theoretical descriptions of the implementation of Stokes' Law in scanning x-ray particle size analyzers may be found in the patents listed above.

The length of time required for an analysis providing data for small particle sizes, e.g., down to 0.1 micron, has remained a problem with such instruments. In prior instruments, the cell must be moved very slowly in order to position it in a timely manner to record accurate data for the continuum of cell positions near the top of the cell. Run times of many hours, depending upon the nature of the sample and the suspending liquid, are the result. Furthermore, the distribution curve must be generated over the same length of time, even if an operator needs only a lower level of precision.

Sample cells for use with sedimentation particle size analyzers are designed to attempt to provide minimum distortion of the x-ray beam by the cell, to provide a bubble-free x-ray path, and to provide maximum dispersion of the sample in the liquid. A problem experienced with current analyzers has been difficulty in obtaining uniform dispersion of sample particles in the suspension prior to the beginning of sedimentation. Sample cells are typically connected via tubing to a mixing chamber, from which the suspension is pumped to the cell. Recirculation of the suspension through the cell and the mixing chamber has been relied upon to maintain a uniform suspension. However, because of interior cell geometry and the location of ports to which the tubing is attached, it has been found that areas of the cell often are not adequately swept by the flow of fluid, and therefore experience some premature settling of larger particles. This can result in an analysis indicating that the sample is finer than it is in fact.

Another problem has been a lack of precise reproducibility of the results obtained for the same sample, particularly from machine to machine of the same type. It is now suspected that the input and output tubing connected to the cell provides horizontal settling channels in which a density gradient can be created. The lighter portion of the suspension at the top of the tubing would have a tendency to rise, and could rise to the top of the cell itself. The presence of less dense material at the top of the cell not resulting from sedimentation in the cell itself would skew the observations taken in that region.

This problem is not as significant in cells which have both inlet and outlet at the top of the cell. However, it is important to have a port at the bottom of the cell to provide better flushing action for the removal of sedimentation deposits.

The introduction of closed-top cells facilitated accurate analysis of very small particles by eliminating the meniscus at the top of the suspension volume and thereby allowing precise determination of the sedimentation height. However, the closed cell created a greater likelihood that bubbles rising to the top of the cell would become trapped in the path of the x-ray beam. Such bubbles falsely reduced the apparent density of the suspension measured by the x-rays, and were quite capable of rendering an analysis useless. As they often were not detected except in the form of obviously flawed output, such bubbles often resulted in the waste of many hours required to re-run the sample.

In prior x-ray particle size analyzers, it is important that the x-ray path through the cell be uniform along the entire scanned height of the cell. The measured transmission of x-rays during a run is used to calculate "percent finer" according to the following equation:

$$\text{Percent finer} = \frac{\ln(I_x/I_o)}{\ln(I_{100}/I_o)},$$

where $I_o$ is the transmittance through the cell containing only the suspending fluid, $I_{100}$ is the transmittance through the cell containing the sample fully suspended before sedimentation, and $I_x$ is the measured transmittance at a height and time during a run. Calibration of the cell requires a determination of $I_o$ and $I_{100}$. If the effect of the cell on the x-rays along the height of the cell is not uniform, $I_o$ and $I_{100}$ will not have a constant value for all measuring heights.

In prior analysers, the construction of the cell has been made to fine tolerances in order to attempt to provide clear windows mounted in exactly parallel relationship to one another. These attempts have not been entirely successful. Furthermore, the cell windows can become dirty in a non-uniform manner, adding to the problem. Some prior analyzers have made a single measurement of $I_o$ and of $I_{100}$ at a selected cell height, and assumed that the cell is sufficiently uniform. Another technique has been to measure $I_o$ and $I_{100}$ at several heights and to accept the average of these measurements as representative of the cell for all calculations of percent finer. All such techniques result in somewhat inaccurate particle size results if there is a significant difference in cell transmittance characteristics at different heights along the cell.

Thus, there has been a need in the art for an x-ray particle size analyzer capable of faster analysis, capable of highly uniform dispersion of the sample prior to sedimentation, not affected by sedimentation in tubing, capable of detecting and eliminating bubbles before the start of a run, and capable of compensating in a meaningful way for nonuniformities in x-ray transmission by the cell.

SUMMARY OF THE INVENTION

The present invention provides a number of novel concepts which solve the above-described problems in prior art x-ray particle size analyzers. An analyzer embodying the present invention provides more accurate, reproducible results, and can provide very rapid analysis when desired. The advantages of the invention follow in part from an abandonment of prior accepted practice of taking transmission data continuously at all cell heights and assigning calibration parameters to the cell as a whole. According to the invention, data is taken only at particular positions along the cell, and each such position is individually calibrated. Presentation of the data in the form of a particle size distribution curve can be accomplished very accurately using interpolation techniques. Other features of the invention include a cell design free of the effects of undesirable density gradients, capable of detecting and removing bubbles, capable of attaining a highly uniform dispersion of sample prior to sedimentation, and including a safety interlock device for blocking x-ray projection when the cell is being accessed.

Generally described, the present invention provides an apparatus and method for acquiring information relating to the distribution of particle sizes in a sample undergoing sedimentation in a suspension of the sample in a fluid medium contained in a sample cell, while passing a photon beam, preferably x-rays, from a radiation source through the suspension of the sample, by moving either the cell or the source to aim the x-ray beam at a first predetermined location along the cell; waiting at the predetermined location until one or more selected times after the beginning of sedimentation; and measuring and recording the transmittance of x-rays through the cell containing the suspension at the one or more selected times. Operation can continue by moving either the cell or the x-ray source to aim the x-ray beam at a second predetermined location along the cell spaced apart from the first predetermined location; waiting at the second predetermined location until an additional one or more selected times after the beginning of sedimentation; and measuring and recording the transmittance of x-rays through the suspension at the one or more selected times. The procedure can be repeated until information has been obtained over a desired range of particle sizes, and a particle size distribution curve can be produced by interpolation between information obtained at the selected times.

The invention also provides a sample cell apparatus for use in a sedimentation particle size analyzer, comprising a sample compartment and a fluid passageway adjacent to one side of the compartment, extending downwardly to enter the side of the compartment from an angle above the horizontal, such that the passageway provides essentially no horizontal settling channel from which low density material can rise to the top of the compartment. The passageway can extend from a height above the bottom of the compartment to enter the compartment even with the bottom of the compartment, and preferably extends downwardly from a height at or above the top of the compartment.

In the preferred embodiment, the sample compartment and fluid passageway are defined within a chamber by a vertical wall extending from the top of the chamber to a point spaced downwardly from the top of the chamber, the wall being tapered at its bottom end to provide angled entry into the sample compartment portion of the chamber.

A capability for cleaning the cell and removing any bubbles can be provided by including means for tilting the compartment in the direction of the passageway and draining the contents of the compartment through the passageway while venting the compartment through a port at the top of the compartment, and means for filling the compartment through the passageway while the compartment is tilted and venting gas from the compartment through the port. To detect and eliminate bubbles automatically, the apparatus can include means for detecting and eliminating bubbles from the compartment, comprising means for measuring the transmission of electromagnetic radiation through the compartment at a plurality of locations along the height of the compartment; means for determining the degree of uniformity of the transmission among the locations; and means responsive to the uniformity determining means for operating the tilting, draining and filling means to re-fill the compartment.

The invention also provides a safety interlock device for a cabinet containing an x-ray source and having a door for providing access to the interior of the cabinet, comprising a plate mounted for pivotal movement about an axis from a blocking position in which the plate prevents x-rays from entering the cabinet to a clear position in which the plate is out of the path of the x-rays; an arm extending from a location on the plate on the opposite side of the axis from the x-ray source; and cam means movable with the door and engaging the arm for moving the plate from the blocking position to the clear position responsive to closing of the door. The device can also include means for urging the plate into the blocking position, and the center of gravity of the plate and arm is preferably spaced apart from the axis, such that the plate normally pivots into the blocking position.

Thus, it is an object of the present invention to provide an improved sedimentation particle size analyzer.

It is a further object of the present invention to provide a sedimentation particle size analyzer which conducts rapid automatic analyses.

It is a further object of the present invention to provide a sedimentation particle size analyzer which compensates for non-uniformities in cell optics.

It is a further object of the present invention to provide a sedimentation particle size analyzer which disperses a sample into a highly uniform suspension prior to sedimentation.

It is a further object of the present invention to provide a sedimentation particle size analyzer which is not affected by density gradients formed in tubing or other settling channels.

It is a further object of the present invention to provide a sedimentation particle size analyzer which collects data in a manner which allows flexible presentation of the analytical results.

It is a further object of the present invention to provide a sedimentation particle size analyzer which detects and eliminates bubbles in the sample cell.

It is a further object of the present invention to provide a sedimentation particle size analyzer which gives highly reproducible results from run to run and from machine to machine.

It is a further object of the present invention to provide an improved sample cell for a sedimentation particle size analyzer.

It is a further object of the present invention to provide a sample cell for a sedimentation particle size analyzer having improved capabilities for draining, filling and debubbling, and which is not subject to problems caused by density gradients in tubing or other settling channels.

It is a further object of the present invention to provide an improved x-ray safety interlock for a sedimentation particle size analyzer.

Other objects, features, and advantages of the present invention will become apparent upon reading the following detailed description of embodiments of the invention, when taken in conjunction with the accompanying drawing and the appended claims.

BRIEF DESCRIPTION OF THE DRAWING

FIG. 1 is a schematic representation of an x-ray particle size analyzer embodying the present invention.

FIG. 2 is a pictorial view of the particle size analyzer with portions broken away to show interior detail.

FIG. 3 is a partial vertical cross sectional view taken along line 3—3 of FIG. 2, showing positions of the movable cell.

FIG. 4 is a partial front plan view of the analyzer taken along line 4—4 of FIG. 3.

FIG. 5 is a side plan view of the cell assembly and cell mounting block.

FIG. 6 is a top plan view of the cell and mounting block of FIG. 5.

FIG. 7 is a side plan view of the safety interlock device of the present invention.

FIG. 8 is a horizontal cross sectional view taken along line 8—8 of FIG. 7.

FIG. 9 is a schematic flow diagram of the sequence for scanning the cell to determine the $I_o$ or $I_{100}$ values for the calibrated cell locations.

DETAILED DESCRIPTION

Referring now to the drawing, in which like numerals refer to like parts throughout the several views, FIG. 1 shows a schematic representation of a sedimentation particle size analyzer 10 embodying the present invention. FIG. 2 is a pictorial view of a preferred embodiment of the analyzer 10, which is preferably contained in a housing 12. Sedimentation of sample particles suspended in a liquid takes place in a sample cell 15. The sample and liquid are mixed together in a mixing vessel or chamber 17 by a magnetic stirrer 20 positioned below the mixing vessel 17. The stirrer 20 rotates a stirrer element positioned within the vessel 17 to thoroughly mix the contents of the vessel.

The contents of the mixing vessel can also be recirculated through a recirculation line 24 which includes a mixing pump 25. The pump 25 can be a unidirectional peristaltic pump. The line 24 includes a liquid inlet valve 28 through which liquid can be drawn from a liquid supply reservoir 27. The line 24 also includes a waste valve 29 through which the contents of the mixing chamber 17 may be routed to waste. In the preferred embodiment, the reservoir 27 and supply valve 28 are located upstream of the pump 25, and the waste valve 29 is located downstream of the pump 25.

The cell 15 is connected to the mixing vessel 17 by two supply lines 33 and 34. The line 33 includes a reversible cell pump 35, preferably a peristaltic pump. Forward and reverse pump directions are shown by arrows F and R in FIG. 1. Operating in a forward direction, the pump 35 supplies liquid (sometimes containing suspended sample) from the vessel 17 to the cell 15, whereas in its reverse direction the pump returns liquid from the cell to the vessel through the line 33. When the cell is filled with fluid, further operation of the pump 35 in a forward direction forces fluid out of the cell into the line 34 and back to the vessel 17. Conversely, reverse operation of the pump 35 can draw fluid from the vessel 17 into the cell 15. The line 34 includes an air valve 37 which vents the line and the cell to atmosphere.

Concentration of the suspension in the cell 15 during sedimentation is measured by passing x-rays from an x-ray source 40 through a first slit 41, the cell 15, and a second slit 42, after which the x-rays are detected by a conventional photodetector 45, such as a geiger counter or photomultiplier tube. The slits are defined in a U-shaped yoke 43 which surrounds the cell on three sides, as shown in FIG. 2. The x-ray source 40 is powered by a conventional power supply 39.

The cell 15 is mounted on a U-shaped cell mounting block 48 best shown in FIGS. 4–6 and described in detail below. The mounting block 48 is positioned for movement by a cell stepping motor 50. The cell moves up and down relative to the x-ray beam during analysis. Those skilled in the art will understand that this scanning of the x-ray beam can also be accomplished by moving the x-ray source rather that the cell. The present invention also provides a means for tilting the sample, which in the preferred embodiment occurs when the sample cell 15 is lowered by the motor 50 below the x-ray beam. A cam surface 52 defined in the bottom portion of the cell mounting block 48 engages a cam follower pin 53. The force of the cam surface on the pin 53 causes the mounting block 48 and cell 15 to tilt about a pivot axis 54, for purposes of filling, recirculating and bubble elimination as described below.

Operation of the sedimentation particle analyzer 10 is controlled by a microcomputer 60, which can be a general purpose personal computer. Conventional interfaces are provided, preferably on a plug-in expansion board (not shown), to operate and monitor the stirrer 20, the pumps 25 and 35, the valves 28, 29 and 37, the cell motor 50, and one or more conventional temperature sensors 62 mounted near the cell. The computer is also interfaced with the photodetector 45 through a period averaging circuit 61, which reads the x-ray intensity data detected by the detector 45. The operation of the period averager 61, which may be placed on the same expansion board, is described below. The x-ray source 40 need not be interfaced with the computer.

Referring now to FIG. 2, the housing 12 defines a cell compartment 70 in which is located an elevator assembly 72. The elevator 72 includes an upper plate 73 and a lower platform 74 held in spaced apart horizontal relation by three columns 76. The columns 76 are hollow and include interior bearings (not shown). Three guide rods 78 pass through the columns 76 and the plates 73 and 74. The guide rods are anchored in the housing 12 at their top and bottom ends. In FIG. 2, the anchor points of the top ends of the rods 78 are not shown.

A drive screw 80, shown in FIG. 3, extends downwardly from the motor 50, mounted above the cell compartment, through a drive nut 81 mounted in the upper plate 73 of the elevator unit 72. Rotation of the screw 80 causes the elevator to move up and down along the guide rods 78. The drive nut 81 and screw 80 are fitted with a conventional anti-backlash device designed to create a precise relationship between the degree of rotation of the screw 80 and the actual motion of the elevator, and therefore of the cell 15.

The cell 15 and mounting block 48 are shown in more detail in FIGS. 4–6. The mounting block 48 consists of two U-shaped halves, 83 and 85, connected by screws 84. When secured together, the halves define in the lower edge of the block 48 the cam surface 52. Also defined is a cavity 86 at the lower corner of the block 48 at which is located the pivot axis 54. A pair of openings 87 pass through the halves 83 and 85 of the block 48 along the pivot axis 54 to communicate with the cavity 86. An anchoring foot 88 is attached to the platform 74 adjacent to the front edge thereof and defines a pair of vertical arms 89 extending up into the cavity 86. A pair of bolts 92 extend from the exterior of the block 48 through the openings 87, through a pair of bearings 93, and are secured in the vertical arms 89. The mounting block 48 is thus pivotable about the bolts 92, which lie along the pivot axis 54. A stop 95 extends downwardly from the bottom surface of the block 48 spaced apart from the pivot axis 54, to engage the platform 74 and maintain the block 48 and cell 15 is a level condition when the cell is above the pin 53, as shown in FIG. 3.

Referring to FIGS. 5 and 6, the cell assembly 15 includes a central plate 100 which has beveled vertical edges 101 on one side and is cut out to define a cell cavity 115. The central plate is sandwiched by a pair of windows 102, of materials well known in the art, and further by a pair of clamping plates 104 which define central cut-outs to expose the portion of the windows covering the cell cavity 115. The assembly is held together by a plurality of screws 105.

The cell assembly 15 fits into the mounting block 48 as shown in FIGS. 5 and 6. The U-shaped half 83 of the block 48 defines a pair of flat shoulders 107 along the inside vertical edges of the "U". The other half 85 defines a beveled shoulder 109 along one of its inside edges, and a set screw 110 is tapped at an angle through the other arm of the "U". Thus, the assembled halves 83 and 85 form a pocket for matingly receiving one vertical side of the cell assembly 15 with one beveled edge 101 engaging the beveled shoulder 109, and the set screw being tightened against the other beveled edge 101. The cell 15 also sits firmly on the lower horizontal portion of the "U" of the block 48. Therefore, when the set screw 110 is tightened, the cell is in a well defined, reproducible position with respect to the rest of the analyzer 10.

The cell cavity 115 defined by the plate 100 has a unique cross sectional shape best shown in FIG. 5. The cavity is generally rectangular, and is connected to the line 33 at the upper corner of the cavity nearest to the pivot axis 54 by a passageway 117, and to the line 34 at the other upper corner by a passageway 118. These passageways may serve as either inlet or outlet passageways depending on the direction of operation of the cell pump 35. The lower corner 119 of the cavity 115 nearest to the pivot axis 54 is rounded. A vertical wall 120 extends downwardly from the top of the cavity 115 and terminates adjacent to the corner 119. The wall 120 is spaced apart a short distance from the side of the cavity to form a channel 122 through which fluid must travel between the main sedimentation compartment of the cavity and the passageway 118. The wall 120 is curved at its end 124 to match the curvature of the corner 119. Fluid entering the cavity 115 from the passageway 118 thus sweeps down the channel 122 and into the bottom of the cavity at a downward angle as shown by the arrow 126 in FIG. 5.

The structure of the cell cavity as just described allows fluid entry at both the top and bottom of the cell for circulation and flushing purposes, but provides virtually no horizontal settling channels in which density gradients might form and affect the density in the main compartment in which the analysis occurs. Because of the angled entry of the channel 122 into the main compartment, any lighter density that does form at the end 124 of the wall 120 will tend to rise up the channel 122 rather than within the main compartment, and therefore will not disrupt the analysis.

A unique safety interlock system 132 is provided in the analyzer 10 to prevent x-rays from entering the cell compartment 70 when access into the compartment 70 is possible. As shown is FIGS. 7 and 8, the cell compartment 70 is fitted with a sliding door 130, preferably made of a transparent plastic material. To provide the interlock, an L-shaped recess 134 is formed in the exterior surface of the side wall 71 of the cell compartment 70 which separates the compartment 70 from the x-ray source 40, as best shown in FIG. 4. An L-shaped rocker member 136 is mounted within the recess 134 to pivot about a pin 140 engaging a horizontal leg 138 of the rocker member 136. The pin 140 is positioned such that the center of gravity of the rocker member 136 is on the side of the pin closest to the door 130. Furthermore, a spring 142 is provided acting against the top of the rocker member 136 to force the rocker member toward the door. Such a position 136a is shown in dotted lines in FIG. 7, and it will be seen that the leg 138 covers the slit 41, preventing x-rays from passing through the slit into the compartment 70.

A plunger 144 is slidably fitted through the housing 12 so as to engage both the door 130 and the rocker member 136. The door 130 is provided with a recessed horizontal cam track 146 along which the plunger 144 travels as the door is opened and closed. As shown in FIG. 8, when the door is closed, the cam track pushes the plunger 144 inwardly against the rocker member 136 and pivots the leg 138 downwardly to its full line position in FIG. 7. This exposes the slit 41 and allows x-rays to pass through the cell 15. When the door is opened, the spring 142 and gravity acting on the rocker member 136 urge the plunger 144 into the cam track 146 (position 144a in FIG. 7), which becomes deep enough to allow the rocker member 136 to pivot to cover the slit 41.

The microcomputer 60 controls the various elements of the system during operation in a manner described below. In a conventional manner, the computer sets and resets bits on the interface expansion board to send signals to operate relays to switch valve positions, switch pumps on or off, and switch the direction and speed of the cell pump. Signals are similarly sent to the cell stepping motor controller to tell it which direction to move the cell, at what speed, and how many steps of the stepping motor 50 to move.

The period averager 61 receives the output from the photodetector 45, but ignores it except when instructed by the computer to read the output. The period averager includes a clock crystal and two counters. A signal is sent from the computer telling the period averager to count a certain number of x-ray photons and to send back the time elapsed during the counting process. One counter of the period averager counts the elapsed time and the other counts down from the predetermined number of x-ray pulses received. When the x-ray count reaches 0, a signal is generated shutting down the x-ray sampling, setting the clock count, and setting a status bit indicating that the task is complete. The computer may then calculate the elapsed period required for receipt of the x-ray data, which represents the transmittance of x-rays through the suspension in the cell, and also the concentration of the sample.

The period averager also receives temperature data for purposes of displaying the current temperature measured by the temperature sensor 62. The signal from the sensor is converted to a voltage and then to a frequency by a frequency conversion circuit 63. The output of the circuit 63 is received by the period averager 61, which measures the reciprocal of the frequency and sends the computer elapsed time data. The computer converts the data to a temperature value that can be displayed on the screen of the computer. The foregoing circuitry performs conversions and calculations the implementation of which is well known to those skilled in the art.

The temperature sensor 62 is also directly connected to the interface expansion board where the signal from the sensor sets or resets a single bit depending upon whether the temperature is within plus or minus one-half degree of the operator-adjusted set point. This signal is used during the operation of the system to determine whether the temperature of the cell environment is stable prior to an analysis, as described below.

OPERATION

Generally, the cell is rinsed and filled with the liquid to be used to suspend the sample, such as water or organic liquid. Then the "beam split" position of the cell with respect to the x-ray beam is determined. This is the position at which the x-ray beam is directed precisely at the very top of the enclosed sample compartment 115, and is taken as the location at which the intensity of the x-ray beam is one-half of the intensity of the unobstructed beam passing through the cell windows. This position is stored as the reference point for determining precise cell locations during movement of the cell, as required for Stokes' Law calculations.

Subsequently, the cell containing particle-free suspending liquid is moved past the x-ray beam to obtain the $I_o$ baseline transmittance data for a plurality of individual cell positions. Analysis data will be taken only at these calibrated data acquisition positions. This scanning procedure is also carried out to determine whether bubbles are present in the cell, and, if so, to eliminate the bubbles by refilling the cell in a tilted orientation. Then the cell is drained and loaded with a suspension of the sample in the liquid. Information necessary for the analysis is input into the computer memory (or recalled from tables in the computer data storage) relating to the sample density, the liquid density and the liquid viscosity. Information is also input concerning the desired accuracy or resolution of the analysis, which affects the speed with which the analysis will be completed.

Meanwhile, the $I_{100}$ calibration data is being obtained by moving the cell containing a 100 percent suspension of the sample to each of the positions for which $I_o$ was measured, and again measuring the x-ray transmittance. Again, the scanning information is used to determine whether bubbles are present. If the cell transmittance is reasonably uniform, the temperature stability of the cell is checked. When the temperature is stable, the computer executes a preprogramming routine to establish the cell positions and times at which data points will be taken. The analysis is commenced by turning off the cell pump 35 and allowing the sample to settle through the liquid. X-ray transmittance is measured at many, but usually not all, of the calibrated cell positions. Several data points may be taken while the cell is stopped at one location. When 250 data points have been taken according to the preprogrammed schedule, the run time is recorded and the cell fluid circulated to resuspend the sediment. If appropriate, the cell is rinsed. Subsequently, the operator calls upon the computer to process the collected data and to prepare graphic or tabular representations of the particle size distribution and other characteristics of the sample.

Referring more particularly to FIG. 9, the routine is described according to which calibration of particular cell locations at which data will be taken is accomplished. The values obtained are stored and used to adjust data actually taken at these locations during particle sample analysis. This procedure obviates the need to rely upon overall estimates of the cell characteristics.

First the status of the cell pump is stored and all valves are closed. Then the cell is moved to the first cell location to calibrated, the x-ray intensity is measured, and the value is stored as either an $I_o$ or an $I_{100}$ value for that location, depending upon whether the cell contains particle-free liquid or a suspension of particles, respectively. This is repeated for all of the locations to be calibrated. Then the standard deviation and average of the measured values are analyzed for uniformity. If they fall within predetermined tolerances, the apparatus may proceed to analysis. If the tolerances are not met, corrective action is taken in the form of draining and refilling the cell to drive out any bubbles that may be responsible for the nonuniformity. Draining and refilling is done with the cell tilted as described above. Then the scanning is begun again at the first location and new data collected for all the locations. If the values still do not meet the tolerances the corrective action is repeated for a total of six scans. If still unacceptable, the operation of the apparatus is terminated and error message is displayed.

Equipment Description

The SediGraph 5100 Particle Size Analysis System 10 consists of either one or two particle size analyzers and a multi-function computer. The particle size analyzer is lightweight and rugged in construction, and maintains performance levels that are superior by any standard. It is designed for completely automatic operation; however, a removable window on the front panel provides convenient observation of, and access to the temperature-controlled analysis compartment. It contains an internal fixed-position X-ray source/detector system and a vertical cell movement assembly. It incorporates a complete plumbing system for circulation of sedimentation liquid and particle sample mixture between the cell, the external mixing chamber, an external sedimentation liquid container, and an external waste container. It also contains a detachable magnetic stirring assembly, which can be replaced with an mechanical stirrer when required.

The computer used with the system is a selected PC compatible (or equivalent). Peripheral equipment includes a keyboard, a video monitor, a dot-matrix printer/plotter, and an optional eightcolor pen plotter. Convenient and easy operation is provided by powerful operating system software in conjunction with a user-friendly, menu-driven particle analysis program.

The SediGraph 5100 Particle Size Analysis System provides fully-automated operation for both particle analysis control and analysis data management.

The Analysis Technique

The Sedigraph 5100 analyzes particle sizes using the sedimentation method. This method is firmly established as one of the most accurate methods known. It is significantly more accurate than those which use laser or photoextinction devices. By measuring the gravity-induced travel rates of different size particles in a liquid with known properties, the particle sizes are determined. The rate at which particles fall through the liquid id described by Stokes' Law. The largest particles fall at the fastest rate, while the smallest particles fall at the slowest rate, until all of the particles have settled and the liquid is clear. Since different particles rarely exhibit a uniform shape, each particle size is reported as an "Equivalent Spherical Diameter." This is the diameter of a sphere of the same material with the same gravitational travel rate.

Sedimentation is accomplished in the Sedigraph 5100 using a finely collimated beam of low energy X-rays and a detector to determine the distribution of particle sizes in a cell containing a sedimentation liquid. The X-ray source and detector assembly remain stationary, while the cell moves vertically between them. The cell contains a transparent window through which X-rays from the source reach the detector. The distribution of particle mass at various points in the cell affects the number of X-ray pulses reaching the detector. This X-ray pulse count is used to derive the particle diameter distribution and the percent mass at given particle diameters.

Features

Single dual analyzer control provides simultaneous and independent operational control and data management for two analyzers in dual-unit system, drastically improving efficiency and reducing analysis backlog. Single-unit system available for improved efficiency in lower volume throughput environments.

Multiple speed operation permits selection of one of three analysis speeds for a broader range of user applications: a high-resolution analysis speed to meet demands for maximum analysis resolution; a medium analysis speed to meet demands for optimal analysis resolution/throughput volume; and an accelerated analysis speed to meet demands for accuracy with increased throughout volumes. Resolution provided at each speed is the highest in the industry.

Multi-task computer control provides both automatic control of operating conditions (for either one or two analysis units) and efficient creation, organization, preservation, and retrieval of analysis data. This increases efficiency and output while decreasing the amount of operator intervention and errors.

User-friendly system operation provides ease of operation and error protection with minimal operator training. Onscreen user information (or "Help") is also provided upon keyboard request.

Plot overlay provides the convenience of displaying analysis data from either different particle samples or the same particle sample on the same graph. Up to four plots, of the same type, for different samples can be provided on the same graph. Up to two plot types (cumulative and population) from the same sample analysis can also be provided on the same graph. This makes comparison of analysis results both convenient and accurate.

Automatic cell profile adjustment eliminates the need for manual adjustments to both the sample cell and to analysis results. In addition, this feature improves the accuracy of analysis results.

Sedimentation liquid data storage saves time and prevents errors in establishing system operating conditions. Up to 50 tables containing sedimentation liquid viscosity and density data may be stored and automatically accessed for interpolation of data to match current cell temperature.

System operating conditions storage saves time, eliminates errors, and maintains consistency in establishing system operating conditions. Up to 50 system operating condition files may be stored and recalled by a single keyboard entry.

Analysis report format storage saves time and eliminates the need to separately request each plot type and/or tabular report type. Up to 50 stored analysis report formats (or "custom" report option sets) may be generated by a single keyboard entry.

Expanded analysis range provides broader equipment application by performing detailed analysis on a wider range of particle sizes: from 300 to 0.1 micrometers.

Complete particle accountability improves the quality and accuracy of particle analysis data, and can be used to indicate the need for further analysis. All particles in the sample cell are accounted for, even those which are outside the operating range of the unit.

X-Y expansion permits the operator to "magnify" segments of plotted analysis results. Plotted segments of the X-axis, the Y-axis, or both may be expanded. This makes the analysis results more informative.

Automatic bubble detection elimination saves time and eliminates both the need for operator intervention and the creation of invalid analysis data. Bubbles in the cell are automatically detected, followed by automatic initiation of the "relentless" bubble elimination process.

Automatic cell fill/purge/rinse eliminates the need for regular removal of cell from the analyzer, and provides closed-loop flushing of particle residue from the cell. Separate pumps automatically control sample mixture suspension and cell loading/unloading.

Concentration level monitor saves time and improves efficiency of operation. The cell mixture concentration levels at the start of the analysis are monitored.

System status display provides increased efficiency and equipment monitoring ease. The operating state of each of up to two analyzers, and the samples analyzed, is always displayed at one source.

Plot type variety enhances the presentation of, and provides flexibility to analysis output. Up to 11 different plot types may be selected for analysis output.

Analysis data archive provides storage of, and instant access to historical analysis data. The output of up to 6,000 analyses (in operator-defined directories) may be stored.

Particle Analysis Control

Single/Dual Analyzer Control

The multi-task computer control of the SediGraph 5100 provides either control of a single analyzer or simultaneous and independent control of two analyzers. The multi-task software provides unmatched operating flexibility. It eliminates problems associated with rigid and complex protocol prevalent in other analysis software. The dual-analyzer control capability results in enormous increases in particle sample throughput and operator productivity. A single-analyzer system may be purchased initially; then, as particle analysis demands increase, a dual-analyzer system can be created simply by purchasing an analyzer—at a fraction of the cost of another company's complete system!

Analysis Speed Control

The SediGraph 5100 provides analysis speed control for each analyzer. Either of three analysis speeds can be selected: a high-resolution analysis speed to meet demands for maximum resolution; a medium analysis speed to meet demands for optimal analysis resolution/-throughput volume; and an accelerated analysis speed to meet demands for accuracy with increased throughput volume. Resolution at either speed selected is the highest provided by a particle size analyzer. The accelerated analysis speed is approximately three times faster than that normally used by sedimentation analyzers; therefore, operating a dual-analyzer system at the accelerated speed could provide a sixfold increase throughput volume.

Automatic Operation

The SediGraph 5100 System is fully automatic in operation. System operating conditions are determined by keyboard entries made to easy-to-understand on-screen menus. To complete a particle sample analysis, all that is required is for the operator to introduce the sample into the mixing chamber, and initiate the analysis with a single keyboard entry. All analysis-dependent parameters, including Reynolds number, are determined automatically. This eliminates errors (frequently encountered in other analysis systems) resulting from manual computation and transposing of analysis values.

User-Friendly Operating Program

The operating software of the SediGraph 5100 System is designed for convenience and ease of operation. The program is menu-driven; therefore, only minimal training is required for the operator. No previous computer experience is necessary for efficient operation. This menu-driven program design provides the operator with both the sequence and available options for establishing system operating conditions. Onscreen user information (or "Help") is accessible to the operator upon request. The operating system also contains provisions for storing common selections of analyzer operating conditions and analysis report options. The operator can access these stored selections with a single keyboard entry. This provides additional convenience and efficiency for both the experienced and the "new", or inexperienced, operator.

Current Operating Status Display

With the SediGraph 5100, the current operating status of the analyzer(s), along with sample analysis information, is displayed on the video monitor. The information is also updated automatically. This provides time savings and monitor-at-a-glance capabilities unmatched by other analysis systems.

Analyzer Operating Conditions Storage

The powerful SediGraph 5100 System computer provides storage of up to 50 "custom" Analyzer Operating Condition sets. This allows the operator to build analysis conditions sets to meet a wide range of demands. The identification number of an Analyzer Operating Conditions set may be entered into the computer via the keyboard prior to a particle sample analysis, and selections contained in the set determine the operating conditions of the analyzer (analysis speed, starting diameter, ending diameter, etc ). Each set can be modified or deleted from storage. This feature saves time and improves efficiency, as the need for the operator to establish routine operating conditions can be eliminated.

Fixed-Position X-ray Source and Detector

During the particle analysis process with the SediGraph 5100 System, the X-ray source and detector assembly remains stationary while the analysis cell moves vertically. Automatic cell positioning is guaranteed, resulting in unmatched accuracy of analysis results. This provides added stability during analyses while maintaining equipment calibration. Some analysis units involve vertical movement of the massive X-ray source and detector assembly. This results in variances in accuracy of analysis results due to uncertainty in positioning the assembly.

Broad Analysis Range

The SediGraph 5100 system determines the particle size distribution of most inorganic powders with particle diameters in the 300 to 0.1 micrometer range. The particles analyzed must be more dense and more absorptive of X-rays than the sedimentation liquid in which they are dispersed. Unlike other systems, the SediGraph 5100 accounts for all particles in the sample cell (even those with diameters outside the analysis range). This improves the accuracy of analysis results. It provides the convenience of indicating that additional analysis steps may be required for particle diameters outside the 5100 analysis range. It also provides the convenience of indicating that a change in either the analysis "start diameter", or the "end diameter", or both, may be required for particle diameters within the 5100 analysis range.

Analysis Temperature Control

The temperature of the particle mixture is controlled by the SediGraph 5100, with temperature variance of 0.2° C. or less for temperatures between ambient +10° C. and 40° C. Ordinarily, analyses are performed at or near 35° C.; however, an analysis may be performed at an elevated temperature. For example, a higher temperature may be used to take advantage of a decrease in viscosity with temperature increase along with the consequent increase in particle sedimentation velocity. The system automatically detects when the particle mixture has reached the specified temperature, establishes the operating conditions for that temperature, and proceeds with the analysis.

Sample Dispersion

The SediGraph 5100 provides a variable speed magnetic stirrer to keep particles in suspension prior to analysis. The stirring speed can be selected to match the requirements of particle suspension, sedimentation liquid viscosity and density. If magnetically susceptible particles are analyzed, the magnetic stirring assembly can be removed and replaced with a mechanical stirrer. If more dispersion energy is required, an ultrasonic probe assembly is available.

Automatic Bubble Detection/Elimination

The SediGraph 5100 automatically detects and removes any air bubbles formed in the analysis cell. Automatic bubble removal is accomplished utilizing a specially-designed deaeration chamber and cell tilt mechanism. This eliminates the need to frequently discard analysis results due to formation of bubbles in the analysis cell, as with other particle size analyzers.

Automatic Cell Profile Adjustment

Prior to each analysis, the SediGraph 5100 examines the analysis cell filled with sedimentation liquid. A baseline is determined, and the cell is examined from bottom to top providing correction for 250 data points. Once particle sample is introduced into the analysis cell, this process is repeated to obtain a full-scale absorption profile. The values obtained during this examination are stored by the computer and used to adjust values derived at the same points during particle sample analysis. This saves time and improves efficiency by eliminating the need for manual thickness adjustments to the analysis cell.

Fast And Automatic Beam Split

The position of the analysis cell relative to the X-ray beam must be known precisely in order for the particle analysis results to be valid. The SediGraph 5100 includes a fast beam split feature which rapidly positions the analysis cell to the point where the X-ray beam intersects the top edge of the cell. As the analysis cell is precision machined, the position of any point on the cell is known to within a few millionths of an inch. The fast beam split data is stored by the computer prior to each analysis and used to determine the precise cell position during the subsequent analysis.

Analysis Data Management

Flexible Data Management

The multi-task capability of the SediGraph 5100 System provides independent control of analyzer operation and analysis data management. Therefore, separate analyses can be performed on two analyzers while reports from either current or previous analyses are being produced. All analysis data (tabular or graphic) can be output to either the video monitor, the dot matrix printer/plotter, the pen plotter, or to other communications devices, as selected by the operator. This saves time and increases the overall output of particle analysis operations. It also provides the flexibility of linking the particle analysis operation with other operations at the same or at different locations.

Sedimentation Liquid Properties Storage

The SediGraph 5100 System computer can store and interpolate density and viscosity information on up to 50 different sedimentation liquids. At some time prior to particle sample analysis, the computer must be supplied with a density and viscosity value for each of up to 50 sedimentation liquids at a high, an intermediate and a low temperature. Each of these sedimentation liquid properties tables is identified by number. At the time of a particle sample analysis, the operator selects the table number which corresponds to the sedimentation liquid used for particle suspension. The powerful computer program determines the density and viscosity value at the current cell temperature at the start of the analysis. This feature eliminates the need for the operator to estimate or determine values. It also saves time and improves efficiency, as the computer determines the values instantly.

Pre-Selected Analysis Points

Up to 29 points in the analysis range can be selected by the SediGraph 5100 operator for tabular reports. The selected points can be either exact equivalent spherical diameters or exact cumulative mass percent coarser/finer values. This feature is quite helpful in comparing a series of reports from different analyses. It is equally helpful in comparing analysis results to adopted standard results.

Report Options Storage

The powerful SediGraph 5100 System computer provides storage of up to 50 "custom" analysis report formats (or Report Options sets). This allows the operator to build analysis data sets to meet a wide range of demands. The identification number of a Report Options set can be entered into the computer via the keyboard prior to a particle sample analysis, and the options contained in the set determine the number and types of graphs/tabular reports produced for that analysis. Each Report Options set can be modified or deleted from storage. This feature saves time and improves efficiency, as the need for the operator to request each graph or tabular report is eliminated.

Data Archiving

The 20 Megabyte computer disk of the SediGraph 5100 System contains space for the complete results of up to 6,000 analyses. Selections can be made to provide the results of any of these analyses can be instantly recalled with a few keyboard entries. Selections can be made to provide the results of any of these analyses as a printed report, to transfer the data to a portable diskette, or even to transmit the data over an RS-232-C line to another computer. This feature provides the convenience of instant access to analysis results. It also provides the convenience of sharing analysis results between different operations or different geographic locations.

Merging Of Other Analysis Data

Detailed analysis data for particles ranging from 300 to 0.1 micrometers in diameter is provided automatically by the SediGraph 5100 System. However, data from other types of analysis (sieve, screen, etc.) for particles ranging from 1,000 to 300 micrometers in diameter can be manually entered into the computer. If data from the SediGraph 5100 analysis is also manually re-entered into the computer at this time, both sets of data are merged. Therefore effective reporting for particles ranging from 1,000 to 0.1 micrometers in diameter is provided. Having four decades of analysis in a single report provides convenience and improves the quality of analysis reports.

Analysis Data Plot Variety

Eleven different plot types are provided by the SediGraph 5100 System. These smooth and distinct plots are provided by a dot matrix printer/plotter. For added convenience, an eight-pen X-Y plotter can also be selected to provide data plots. In addition, segments of either the X-axis or the Y-axis, or both, can be expanded to provide more detail concerning those segments. The plot types provided include:
  Cumulative Mass Percent Finer
  Cumulative Mass Percent Coarser
  Cumulative Number per Gram Coarser
  Cumulative Surface Area per Gram Coarser
  Log Probability
  Population Mass Percent (Differential)
  Population Mass Percent (Histogram)
  Population Number Percent Finer (Differential)
  Population Number Percent Finer (Histogram)
  Population Surface Area per Gram (Differential)
  Population Surface Area per Gram (Histogram)

Plot Overlay

The SediGraph 5100 provides the capability of overlaying up to three plots of the same type onto a fourth plot. These plots are recalled from the analysis data of three different particle samples in the data archive. For example, the cumulative mass percent curve for each of three different particle samples can be plotted over the same type curve of a fourth sample. The SediGraph 5100 also provides the capability of overlaying one plot type onto a different plot type from the same sample analysis results. For example, a particle population histogram can be plotted over a cumulative mass percent curve to provide more detailed information. This feature provides convenient and accurate comparison of analysis data from different particle samples. It also provides a convenient and accurate display of more than one kind of analysis data for the same particle sample.

Real-Time Display

When desired, the SediGraph 5100 operator can have a real-time cumulative mass plot of the current analysis displayed on the video monitor. This allows the operator to monitor the progress of, and make immediate procedural determinations concerning current analysis results.

Multiple Report Copies

The SediGraph 5100 System can provide analysis reports to the video monitor, the dot matrix printer/plotter, or over RS-232-C data lines to another computer. When the dot matrix printer/plotter is selected as the report source, the number of report copies automatically produced (up to ten) can be selected by the operator. This feature saves time and improves efficiency, as the need to request each report copy is eliminated.

Application

To provide fast and accurate particle size analyses and analysis data output, the SediGraph 5100 is designed for a wide range of particles. These include:

Abrasives

Aluminum Oxide; Emery; Flint; Garnet; Iron Oxide; Silicon Carbide; Titanium Carbide; Tungsten Carbide;

Pigments

Barium Sulfate; Cobalt Aluminate; Copper Hydroxides; Chromium Oxides; Kaolin; Lead Oxides; Iron Oxide; Nickel Titanium; Titanium Dioxide

Metal Powders

Aluminum; Platinum; Copper; Ruthenium; Gold; Silver; Iron; Stainless Steel; Molybdenum; Tantalum; Palladium; Tungsten

Metal Oxides

Copper Oxides; Ruthenium Dioxide; Manganese Oxide; Uranium Dioxide; Magnesium Oxide; Vanadium Oxide; Nickel Oxide; Zinc Oxide; Plutonium Oxides; Zirconium Oxide

Minerals

Andalusite; Limestone; Barite; Marble; Bauxite; Mica; Borax; Potash; Cinnabar; Pyrite; Clays; Shale; Dolmmite; Silica; Fluorspar; Soils; Galena; Sulfur; Garnet; Talc; Gypsum; Uraninite; Hydroxyapatite; Wollastonite; Kyanite; Zircon

Miscellaneous

Aluminum Trihydrate; Lead Titanate; Aluminum Chlorohydrates; Lead Zirconate; Asbestos (chopped); Lime; Barium Chromate; Mullite; Barium Sulfate; Pesticides; Barium Titanate; Phosphorus; Calcium Carbide; Portland Cement; Calcium Silicate; Potassium Perchlorate; Catalysts; River & Ocean Sediments; Ceramic Slips; Silicon; Calomel; Silver Halides; Fly Ash; Sodium Bicarbonate; Glass Powders; Tricalcium Phosphate; Herbicides; Zirconium Silicate

Specifications

Particle Diameter Range: 300 to 0.1 micrometers Equivalent Spherical Diameter

Resolution: The sedimenting sample is scanned in a narrow beam—less than 0.2% of the total distance scanned permitting high resolution Wetted Materials: Stainless steel, Teflon(R) impregnated alumina/aluminum, Homalite(R) and Viton(R), vinyl, silicone rubber, Kalrez(R), or Tygon (R) tubing Sample Size: 50 mL of dispersed sample—precise concentration is not required Sedimenting Liquids: Any liquid compatible with sample cell materials and not highly absorptive of X-rays (typical liquids are water, glycols, kerosene, mineral oils, alcohols, hexane, mineral spirits, etc.)

Power Requirements: 100 VAC 50/60 Hz, 120 VAC 50/60 Hz, 200 VAC 50/60 Hz; and 240 VAC 50/60 Hz; power selection made at internal power connector Sedimentation Liquids: A wide range of sedimentation liquids can be used for particle analysis with the SediGraph 5100 System. For added convenience, Micromeritics offers the Sedisperse Liquids Series, a complete line of liquids for particle sample analysis. These liquids are available in both aqueous and organic formulations, and are formulated to disperse particles at low solids concentrations. They contain various surfactants, and are effective in dispersing most materials.

We claim:

1. A safety interlock for a cabinet adjacent to an x-ray source and having a door for providing access to the interior of said cabinet, comprising:

a plate mounted for pivotal movement about an axis from a blocking position in which said plate prevents x-rays from entering said cabinet and a clear position in which said plate is out of the path of the x-rays;

an arm extending from a location on said plate to the opposite side of said axis from said x-ray source; and cam means movable with said door and engaging said arm for moving said plate from said blocking position to said clear position responsive to closing of said door.

2. The device of claim 1, further comprising means for urging said plate into said blocking position.

3. The device of claim 1, wherein the center of gravity of said plate and arm is spaced apart from said axis, such that said plate normally pivots into said blocking position.

* * * * *